United States Patent [19]
Lee

[11] Patent Number: 5,187,085
[45] Date of Patent: Feb. 16, 1993

[54] NUCLEIC ACID SEQUENCE ANALYSIS WITH NUCLEOSIDE-5′-O-(1-THIOTRIPHOSPHATES

[75] Inventor: Linda G. Lee, Palo Alto, Calif.

[73] Assignee: Applied Biosystems, Inc., Foster City, Calif.

[21] Appl. No.: 590,218

[22] Filed: Sep. 28, 1990

[51] Int. Cl.$^5$ .............................................. C12Q 1/68
[52] U.S. Cl. ........................................ 435/91; 435/6;
435/968; 436/501; 436/800; 935/78; 935/88
[58] Field of Search ............... 435/6, 91, 172.3, 968;
436/501, 800, 811; 935/78, 88

[56] References Cited
PUBLICATIONS

Tabor et al, proc. Natl. Acad. Sci., vol. 86, pp. 4076–4080 (1989).
Tabor et al, Proc. Natl. Acad. Sci., vol. 84, pp. 4767–4771 (1987).
Innis et al, Proc. Natl. Acad. Sci., vol. 85, pp. 9436–9440 (1988).
Connell et al, BioTechniques, vol. 5, pp. 342–348 (1987).
Smith et al, Meth. Enzymol., vol. 155, pp. 260–301 (1987).
Eckstein, Ann Rev. Biochem., vol. 54, pp. 367–402 (1985).
Eckstein et al, TIBS, vol. 14, pp. 97–100 (1989).
Ansorge et al, Nucleic Acids Research, vol. 15, pp. 4593–4602 (1987).
Prober et al, Science, vol. 238, pp. 336–341 (1987).
Kambara et al, Biotechnology, vol. 6, pp. 816–821 (1988).
Labeit et al, DNA, vol. 5, pp. 173–177 (1986).
Tabor et al, J. Biol. Chem., vol. 265, pp. 8322–8328 (1990).

*Primary Examiner*—Amelia Burgess Yarbrough
*Attorney, Agent, or Firm*—Stephen C. Macevicz

[57] ABSTRACT

A chain-termination method of nucleic acid sequence determination is provided wherein nucleoside triphosphate precursors are replaced with their 1-thiotriphosphate analogs in the polymerization step. This substitution results in more uniform bands of electrophoretically separated DNA fragments which, in turn, results in more accurate base determination.

20 Claims, 4 Drawing Sheets

NUCLEIC ACID SEQUENCE ANALYSIS WITH NUCLEOSIDE-5'-O-(1-THIOTRIPHOSPHATES)

FIELD OF THE INVENTION

The invention relates generally to nucleic acid sequence analysis, and more particularly, to use of nucleoside-5'-O-(1-thiotriphosphates) as DNA polymerase substrates in chain-termination approaches to DNA sequencing.

BACKGROUND

The ability to determine DNA sequences is crucial for understanding the function and control of genes and for applying many of the basic techniques of molecular biology. Native DNA consists of two linear polymers, or strands of nucleotides. Each strand is a chain of nucleosides linked by phosphotidester bonds. The two strands are held together in an antiparallel orientation by hydrogen bonds between complementary bases of the nucleotides of the two strands: deoxyandenosine (A) pairs with thymidine (T) and deoxyguanosine (G) pairs with deoxycytidine (C).

Presently there are two basic approaches to DNA sequence determination: the dideoxy chain termination method, e.g. Sanger et al, *Proc. Natl. Acd. Sci.,* Vol. 74, pgs, 5463–5467 (1977); and the chemical degradation method, e.g. Maxam et al, *Proc. Natl. Acad. Sci.,* Vol. 74, pgs. 560–564 (1977). The chain termination method has been improved in several ways, and serves as the basis for all currently available automated DNA sequencing machines, e.g. Sanger et al, *J. Mol. Biol.,* Vol. 143, pgs, 161–178 (1980); Schreier et al. *J. Mol. Biol.,* Vol. 129, pgs, 169–172 (1979); Mills et al, *Proc. Natl. Acad. Sci.,* Vol. 76, pgs, 2232–2235 (1979); Smith et al, *Nucleic Acids Research,* Vol. 13, pgs, 2399–2412 (1985); Smith et al., *Nature,* Vol. 321, pgs, 674–679 (1987); Prober et al, *Science,* Vol. 238, pgs, 336–341 (1987), Section II, *Meth. Enzymol.,* Vol. 155, pgs, 51–334 (1987); Church et al, *Science,* Vol. 240, pgs, 185–188 (1988); Tabor et al, *Proc. Natl. Acad. Sci.,* Vol. 84, pgs, 4767–4771 (1987); Tabor et al, *Proc. Natl. Acad. Sci.,* Vol. 86, pgs, 4076–4080 (1989); Innis et al., *Proc. Natl. Acad. Sci.,* Vol. 85, pgs, 9436–9440 (1988); and Connell et al., Biotechniques, Vol. 5, pgs, 342–348 (1987).

Both the chain termination and chemical degradation methods require the generation of one or more sets of labeled DNA fragments, each having a common origin and each terminating with a known base. The set or sets of fragments must then be separated by size to obtain sequence information. In both methods, the DNA fragments are separated by high resolution gel electrophoresis. Usually, the DNA fragments are labelled by way of radioactive nucleoside triphosphate precursors or by way of fluorescent dyes.

In most automated DNA sequencing machines, fragments having different terminating bases are labeled with different fluorescent dyes, which are attached either to a primer, e.g. Smith et al (1987, cited above), or to the base of a terminal dideoxynucleotide, e.g. Prober et al (cited above). The fluorescently labeled fragments are combined and loaded onto the same gel column for electrophoretic separation. Base sequence is determined by analyzing the fluorescent signals emitted by the fragments as they pass a stationary detector during the separation process.

Such analysis has been complicated by a number of phenomena, such as band compression, overlapping emission bands of the fluorescent labels, the appearance of artifactual bands, noise due to misincorporation of labeled dideoxynucleosides, and bands that vary widely in intensity in a highly sequence dependent manner, e.g. Mills et al (cited above), Connell et al (cited above), and Tabor et al (1987 and 1989, cited above). The latter two phenomena are believed to be caused by difficulties that some DNA polymerases have in reading through certain template sequences and/or in accommodating some commonly used nucleoside analogs. Band uniformity has been improved in many instances by the use of a modified T7 DNA polymerase (Sequenase TM) and the substitution of $Mn^{+2}$ for $MG^{+2}$ as the divalent cation in the polymerase reactions, Tabor et al (1987 and 1989, cited above). However, the problem persists and still presents an important limitation to current automated DNA sequencing approaches.

SUMMARY OF THE INVENTION

The invention relates to chain-termination methods of DNA sequence analysis wherein different sized DNA fragments are polymerized from nucleoside-5'-O-(1-thiotriphosphate) precursors. The invention in based in part on the discovery that the use of such precursors in place of the usual nucleoside triphosphate precursors (i) leads to fewer sequence-specific pauses in polymerization, (ii) leads to more uniform populations of DNA fragments during polymerization which, in turn, leads to bands of more uniform size during electrophoretic separation, and (iii) eliminates the need to use nucleoside analogs in place of deoxyguanosine triphosphate whenever fluorescein-labelled dideoxynucleotides are employed as chain-terminating nucleotides. Preferably, the method employs the modified T7 DNA polymerase and $Mn^{+2}$ as taught by Tabor et al (1987 and 1989, cited above).

As used herein the term "chain terminating nucleotide" refers to a nucleotide or analog thereof which prevents further polynucleotide chain elongation, or extension, after it has been incorporated into a growing DNA chain by a nucleic acid polymerase. Usually, the chain terminating property of such nucleotides is due to the absence or modification of the 3' hydroxyl of the sugar moiety. Preferably, the chain-terminating nucleotides are 2',3'-dideoxynucleotides.

As used herein the term "spectrally resolvable" in reference to a set of dyes means that the fluorescent emission bands of the dyes are sufficiently distinct, i.e. sufficiently non-overlapping, that target substances to which the respective dyes are attached, e.g. polynucleotides, can be distinguished on the basis of the fluorescent signal generated by the respective dyes by standard photodetection systems, e.g. employing a system of band pass filters and photomultiplier tubes, or the like, as exemplified by the systems described in U.S. Pat. Nos. 4,230,558, 4,811,218, or the like, or in Wheeless et al, pgs. 21–76, in *Flow Cytometry: Instrumentation and Data Analysis* (Academic Press, New York, 1985).

As used herein, the term "bands" includes any spacial grouping or aggregation of polynucleotide on the basis of similar or identical physiochemical properties. Usually bands arise in the separation of labelled DNA fragments by gel electrophoresis.

DETAILED DESCRIPTION OF THE INVENTION

The basic steps of the chain-termination approach to DNA sequencing are (1) providing an oligonucleotide primer and a template nucleic acid containing, as a subsequence, a target nucleic acid whose sequence is to be determined, (2) hybridizing the oligonucleotide primer to the template nucleic acid, (3) extending the primer with a nucleic acid polymerase, e.g. T7 DNA polymerase, Sequenase TM, a reverse transcriptase, or the like, in a reaction mixture containing nucleoside triphosphate precursors and at least one chain terminating nucleotide to form a nested series of DNA fragment populations, such that very shorter DNA fragment is a subsequence of very longer DNA fragment and such that each DNA fragment of the same size terminates with the same chain-terminating nucleotide, (4) separating the DNA fragment populations according to size, and (5) identifying the chain-terminating nucleotide associated with each DNA fragment population. As used herein, the term "nucleoside triphosphate precursors" refers to deoxyadenosine triphosphate (ATP), deoxycytidine triphosphate (CTP), deoxyguanosine triphosphate (GTP), and thymidine triphosphate (TTP), or analogs thereof, such as deoxyinosine triphosphate (ITP), 7-deazadeoxyguanosine triphosphate, and the like. The details of each of the above steps varies according to several factors well known in the art, including the nature of the labelling means for identifying the different chain-terminating nucleotides, the means for separating the different DNA fragment populations, the manner in which the template nucleic acid is provided for the hybridization step, and the like. For example, if the DNA fragment populations are identified by fluorescent dyes attached to primers, then four different primers are provided, each having a different fluorescent label, and the primers are extended in four separate reaction mixtures corresponding to the four different chain-terminating nucleotides. Or, if the DNA fragment populations are identified by the incorporation of radioactively labelled nucleoside triphosphates during the extension step, then the step of extending usually includes four separate reaction mixtures each containing a different chain-terminating nucleotide and the step of separating usually includes separating the DNA fragment populations of each reaction mixture separately according to size. Generally, the references cited in the second paragraph of the Background section disclose the steps of DNA sequencing and their important variations. Accordingly, these references are incorporated by reference.

Preferably, the different DNA fragment populations are identified by fluorescent dyes attached to the chain-terminating nucleotides. Accordingly, in the method of the invention a primer is extended by a DNA polymerase in a reaction mixture containing the four 1-thiotriphosphate analogs of ATP, CTP, GTP, and TTP, and four chain-terminating nucleotides, each labelled with a different member of a set of spectrally resolvable fluorescent dyes, e.g. as disclosed by Fung et al., U.S. Pat. No. 4,855,255; Prober et al (cited above); or the like.

The 1-thiotriphosphate analogs of ATP, CTP, GTP, and TTP are a well known subset of a general class of compounds referred to as nucleoside phosphorothioates, which have been extensively used in enzymology, e.g. Eckstein, Ann. Rev. Biochem. Vol. 54, pgs, 367–402 (1985); and Eckstein et al, Trends in Biochemical Science, Vol. 14, pgs, 97–100 (1989). The nucleoside-5'-O-(1-thiotriphosphates) are commercially available, e.g. Amersham (Arlington Heights, Ill.) or may be synthesized in accordance with Ludwig et al, J. Org. Chem., Vol. 54, pgs. 631–635 (1989).

A template is provided in accordance with the teachings in the art, e.g. Technical Manual for Model 370A DNA Sequencer (Applied Biosystems, Inc., Foster City, Calif.). For example, the target sequence may be inserted into a suitable cloning vector, such as the replicative form of an M13 closing vector, which is then propagated to amplify the number of copies of the target sequence. The single-stranded form of M13 is isolated for use as a template. Alternatively, a template can be provided by polyermerase chain reaction (PCR) as taught in the art, e.g. Innis et al, (cited above); Wilson et al, Biotechniques, Vol. 8, pgs 184–189 (1990); Gyllensten, Biotechniques, Vol. 7, pgs, 700–708 (1989); and the like. After amplification, the template can be used in the polymerization reaction(s) either in liquid phase or attached to a solid phase support, e.g. as taught by Stahl et al, Nucleic Acids Research, Vol. 16, pgs, 3025–3038 (1988); Hultman et al, Nucleic Acids Research, Vol. 17, pgs, 4937–4946 (1989); or the like.

Primers for the method of the invention either can be synthesized on a commercial DNA synthesizer or can be purchased alone or as components in DNA amplification and/or sequencing kits, e.g. United States Biochemical Corporation (Cleveland, Ohio), Clontech (Palo Alton, Calif.) or the like. The step of hybridizing the primer to the template is fully disclosed in the cited references, which provide detailed guidance for application to any particular embodiment of the present invention.

Preferably, the fluorescently labelled chain-terminating nucleotides of the invention have the following form:

XTP—L—R wherein XTP is a chain-terminating nucleoside triphosphate; R is a fluorescent dye; and L is a linking group between the base of the nucleoside triphosphate and the fluorescent dye.

XTP is an analog of the natural nucleoside triphosphate substrate of the DNA polymerase employed which prevents further chain elongation after incorporation. Several such analogs are available for each of the four natural nucleoside triphosphates, e.g. Hobbs et al (cited above) gives a list. Preferably, XTP is a 2',3'-dideoxynucleoside triphosphate. More preferably, XTP is selected from the group consisting of 2',3', dideoxy-7-deazaadenosine triphosphate, 2',3'-dideoxycytidine triphosphate, 2',3'-dideoxy-7-deazaguanosine, 2',3'-dideoxyuridine triphosphate, and 2',3'-dideoxy-7-deazainosine triphosphate. As used herein, the term "dideoxynucleoside" includes nucleoside analogs whose sugar moieties are either cyclic or acyclic. Con- ventional numbering is used whenever specific carbon atoms of a base or sugar of a nucleoside are referred to, e.g. Kornberg, *DNA Replication* (Freeman, San Francisco, 1980).

L can take on a number of different forms such that the length and rigidity of the linkage between the dideoxynucleotide and the dye can vary greatly. For example, several suitable base labeling procedures have been reported that can be used with the invention, e.g. Gibson et al, Nucleic Acids Research, Vol. 15, pgs, 6455–6467 (1987); Gebeyehu et al, Nucleic Acids Research, Vol. 15, pgs, 4513–4535 (1987); Haralambidis et al., Nucleic Acids Research, Vol. 15, pgs, 4856–4876 (1987); and the like. Preferably, L is formed by reacting an N-hydroxysuccinimide (NHS) ester of a dye of the invention with an alkynylamino-derivatized base of a dideoxynucleotide. In this case, L is taken as the moiety between (1) the 5- or 6- carbon of the rhodamine and (2) the carbon of the base to which the rhodamine is attached. Preferably, L is 3-carboxyamino-1-propynyl. The synthesis of such alkynylamino-derivatized dideoxynucleotides of cytosine, thymine, and adenine is taught by Hobbs et al in European patent application number 87305844.0 and Hobbs, J. Org. Chem., Vol. 54, pg, 3420 (1989), which are incorporated herein by reference. Briefly, the alkynylamino-derivatized dideoxynucleotides are formed by placing the appropriate halodideoxynucleoside (usually 5-iodopyrimidine and 7-iodo-7-deazapurine dideoxynucleosides as taught by Hobbs et al (cited above)) and Cu(I) in a flask, flushing with Ar to remove air, adding dry DMF, followed by addition of an alkynylamine, triethylamine and Pd(O). The reaction mixture can be stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flush-chromatography on silica gel using a methanol-methylene chloride gradient. The triphosphates are obtained by standard techniques.

Synthesis of the alkynylamine-derivatized dideoxyguanosine according to the above references requires specially modified quanine precursor (6-methoxy-2-methylthio-7-deazapurine, X), which is obtained from the starting material, 6-hydroxy-2-methylthio-7-diazapurine, XX. Conversion of XX to 6-chloro-2-methylthio-7-deazapurine, XXX, according to Robins and Noell (J. Heterocyclic Chem., Vol. 1, pg, 34 (1964)), followed by displacement of the chloro substituent with methoxide (sodium salt in refluxing methanol) yields X:

A spectrally resolvable set of rhodamine dyes that can be used with the invention consists of tetramethylrhodamine, rhodamine X, rhodamine 110, and rhodamine 6G, which are defined by Formulas 1-4, respectively. Throughout, the *Colour Index* (Association of Textile Chemists, 2nd Ed., 1971) carbon numbering scheme is used, i.e. primed numbers refer to carbons in the xanthene structure and unprimed numbers refer to carbons in the 9'-phenyl.

Formula 1

Formula 2

Formula 3

Formula 4 wherein:

A is a group, such as carboxyl, sulfonyl, or amino, that may be converted into a linking functionality; and B is an anionic acidic group, preferably carboxyl or sulfonyl, and most preferably carboxyl.

Rhodamine NHS esters are synthesized in accordance with the teachings of U.S. Pat. application No. 06/941,985. Important features of the method of synthesizing the rhodamine NHS esters include (1) the reaction condition of having substantially stoichiometric amounts of di-N-succinimidylcarbonate (DSC) and 4-dimethylaminopryidine (DMAP) present for esterification of the 5- or 6-forms of the rhodamine dyes to produce high yields of product at room temperature, and (2) the treatment of the freshly synthesized product with an acidic compound, preferably having a $pK_a$ or less than 5, to prevent conversion back into reactants. The general reaction scheme of the invention is defined by Formula 5:

The methods comprise reaction the acid form of a 5- or 6-carboxylrhodamine (either as a mixture of isomers, or as pure isomers) with equivalent amounts of DSC and DMAP in a polar aprotic solvent to form the carboxyl N-hydroxysuccinimide ester. Suitable polar aprotic solvents include N,N-dimethylformamide (DMF), pyridine, hexamethylphosphoramide (HMPA), or the like. Most preferably, DMF is used as the reaction solvent. The isomerically mixed NHS esters can be separated into their individual isomers for further use. Most preferably, in order to conserve reagents, the acid forms of the 5- or 6-carboxylrhodamines are first separated into their individual isomers by standard separative techniques, e.g. Edmundson et al., Molecular Immunology, Vol. 21, pg. 561 (1984), and then the individual 5- or 6-carboxyl isomers are reacted as described above to form the 5- or 6-carboxyl NHS esters, respectively, which are separated from the reaction mixture, again using standard techniques.

Preferably, the freshly synthesized rhodamine NHS ester is treated with a volatile, organic-soluble acid with $pK_a<5$; and more preferably, a volatile, organic-soluble acidic compound with $pK_a<1$, such as HCl or HBr in methanol, or most preferably, trifluoracetic acid.

Some isomeric mixtures of rhodamine dyes for use with the invention are available commercially, e.g. Molecular Probes, Inc. (Eugene, Oreg.), and others can be synthesized in accordance with the teachings of U.S. Pat. Nos. 2,242,572; 2,153,059; 3,822,270; 3,932,415; and 4,005,092, all of which are incorporated by reference.

Preferably, a spectrally resolvably set of fluorescein-labelled chain-terminating nucleotides are employed with the method of the invention. Many fluorescein dyes are commercially available, e.g. from Molecular Probes, Inc. (Eugene, Oreg.), or Research Organics (Cleveland, Ohio), or can be synthesized by techniques known in the art, e.g., Ghatak et al, J. Ind. Chem. Soc., Vol. 6, pgs, 465–471 (1929); and Khanna et al, U.S. Pat. No. 4,439,356. Alternatively, fluorescein analogs can be synthesized by reacting substituted resorcinol with substituted benzophenone or with substituted trimellitic acid in the presence of propionic acid, in reactions well known in the art. Sulfonylfluoresceins are synthesized following the methods disclosed by Lee et al, Cytometry, Vol. 10, pgs, 151–164 (1989), modified by substituting appropriate reactants to give 5- or 6-carboxyl- or sulfonylfluorescein products. Preferably, when labeling polynucleotides in DNA sequencing the 5- and 6-isomers of the dyes are used separately because they typically have slightly different electrophoretic mobilities that can lead to band broadening if mixtures of the isomers are used. The 5- and 6- isomers of the dyes are readily separated by reverse phase HPLC, e.g. Edmundson et al (cited above). Generally, it is believed that the first eluting peak is the 6- isomer and the second eluting peak is the 5-isomer. Preferably, NHS-esters of the fluorescein dyes are reacted with an appropriate linking functionality on the dideoxynucleotides to form the labelled dideoxynucleotides.

Preferably, the following set of spectrally resolvable fluorescein dyes are employed with the method of the invention: fluorescein ("FAM"); 2',7'-dichlorofluorescein ("2',7'-dichloroFAM"); 2',7'-dimethoxy-4',5'-dichloro-4,7-dichlorofluorescein ("LOU"); and 1',2',7',8'-dibenzo-4,7-dichlorofluorescein ("NAN"), wherein the numbering corresponds to the Color Index numbering scheme for fluorescein dyes. More preferably, FAM is linked to dideoxythymidine through its 6 carbon ("ddT-6-FAM"); 2',7'-dichlorofluorescein is lined to dideoxycytidine through its 5 carbon ("ddC-2',7'-dichloro-5-FAM"); LOU is lined to dideoxyadenosine through its 5 carbon ("ddA-5-LOU"); and NAN is linked to dideoxyguanosine through its 5 carbon ("ddG-5-NAN"). More preferably, the following fluorescein-labelled dideoxynucleotides are employed:

Formula 6 ddA-5LOU

Formula 7 ddC-2',7'-dichloro-5FAM

Formula 8 ddG-5NAN

Formula 9 ddT-6FAM

Preferably, the labelled DNA fragments generated in the polymerization reaction(s) are separated according to size by gel electrophoresis, e.g. Gould and Matthews, cited above; Rickwood and Hames, Eds., *Gel Electrophoresis of Nucleic Acids: A Practical Approach*, (IRL Press Limited, London, 1981); or Osterman, *Methods of Protein and Nucleic Acid Research*, Vol. 1 (Springer-Verlag, Berlin, 1984). Preferably the type of gel is polyacrylamide having a concentration (weight to volume) of between about 2–20 percent. More preferably, the polyacrylamide gel concentration is between about 4–8 percent. Preferably the gel includes a strand separating, or denaturing, agent. Detailed procedures for constructing such gels are given by Maniatis et al., in *Methods in Enzymology*, Vol. 65, pgs. 299–305 (1980); Maniatis et al., *Biochemistry*, Vol. 14, pgs. 3787–3794, (1975); and Maniatis et a., *Molecular Cloning: A Laboratory Manual* (Cold Spring Harbor Laboratory, N.Y., 1982), pgs. 179–185. Accordingly these references are incorporated by reference. The optimal gel concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations. Preferably, during polynucleotide chain extension deoxyinosine triphosphate is substituted for deoxyguanosine triphosphate to avoid so called "band compression" during electrophresis, e.g. Mills et al, Proc. Natl. Acad. Sci., Vol. 76, pgs, 2232–2235 (1979). By way of example, polynucleotides having sizes in the range of between about 10–500 bases are separated and detected in accordance with the invention in the following gel: 6 percent polyacrylamide made from 19 parts to 1 part acrylamide to bis-acrylamide, formed in a Tris-borate EDTA buffer at pH 8.3 (measured at 25° C.) with 48 percent (weight-/volume) urea. The gel is run at about 40° C.

The bands of fluorescently labelled DNA fragments on the gel are illuminated by standard means, e.g. high intensity mercury vapor lamps, lasers, or the like. Preferably, the bands are illuminated by laser light generated by a argon ion laser, particularly the 488 and 514 nm emission lines of an argon ion laser. Several argon ion lasers are available commercially which laser simultaneously at these lines, e.g. Cyonics, Ltd. (Sunnyvale, Calif.) Model 2001, or the like.

An important feature of the invention is the nucleic acid polymerase used for chain extension in the DNA sequencing procedure. Preferably, the polymerase used in the method of the invention is the modified T7 DNA polymerase (Sequenase TM) with a manganese buffer, described by Tabor et al, proc. Natl. Acad. Sci., Vol. 86, pgs, 4076–4080 (1989). In further preference, the polymerization reaction mixtures also contain pyrophosphatase as taught by Tabor et al, J. Biol. Chem., vol. 265, pgs, 8322–8328 (1990), which reference is incorporated by reference.

EXAMPLES

The following examples serve to illustrate the present invention. The concentrations of reagents, temperatures, and the values of other variable parameters are only to exemplify the invention and are not to be considered limitations thereof.

EXAMPLE 1

6-TMR-NHS

6-TMR acid was separated from a mixture of the 5- and 6-TMR acid isomers by column chromatography. 8.82 mg of 6-TMR acid and 10.5 mg of DSC were dissolved in 0.5 ml of dry DMF under argon. 0.09 ml of a 0.5 molar solution of DMAP in tetrahydrofuran (THF) was added in one portion. After 2 hours at room temperature, the mixture was taken into 50 ml of chloroform and washed three times with a 1:1 solution of brine:water. The chloroform was evaporated and the residue was purified on a 20 g silica gel column (300:30:8 methylene chloride:methanol:acetic acid elution). Fractions with $R_f$ of about 0.4 were evaporated to dryness, yielding 8.6 mg of 6-TMR-NHS as its acetic acid salt.

EXAMPLE 2

6-ROX-NHS

6-ROX acid was separated from a mixture of 5- and 6-acid isomers by column chromatography. 46.2 mg of 6-ROX acid and 58 mg of DSC were dissolved in 2 ml of dry DMF under argon and 0.45 ml of a 0.5 molar solution of DMAP in THF was added in one portion. After 1.5 hours at room temperature, the mixture was taken into 100 ml chloroform and washed four times with a 1:1 solution of brine:water. The chloroform was evaporated and the residue was purified on a 40 g silica gel column (300:30:8 methylene chloride:methanol:acetic acid elution). Fractions with $R_f$ of about 0.5 were evaporated to dryness, yielding 56.4 mg of 6-ROX-NHS as its acetic acid salt.

EXAMPLE 3

A Stable Formulation of Rhodamine NHS esters a) 0.44 mg of 6-carboxy-X-rhodamine NHS ester from Example 3 and 80 ul of 0.01 molar ethanol amine in methanol were combined. Reverse phase HPLC of the reaction mixture with acetonitrile and 0.1 molar triethylammonium acetate buffer (pH=7.0) showed that the product was composed of 70% X-rhodamine acid and 30% of X-rhodamine NHS ester (observed as the ethanolamide of 6-carboxy-X-rhodamine from its reaction with ethanol amine).

b) 0.15 g of 6-carboxy-X-rhodamine NHS ester from Example 3 were dissolved in 100 m. of chloroform; the chloroform solution was washed two times with 0.5 molar sodium bicarbonate, dried with sodium sulfate, filtered, treated with 0.1 ml of acetic acid and evaporated to dryness. 0.35 mg of the product was treated exactly as in a); reverse phase HPLC showed 20% 6-carboxy-X-rhodamime acid and 80% of 6-carboxy-X-rhodamine NHS ester.

c) 0.15 g of 6-carboxy-X-rhodamine NHS ester from Example 3 was treated exactly as in b), except that trifluoroacetic acid was substituted for acetic acid. 0.19 mg of the resulting solid were treated exactly as in a); reverse phase HPLC showed <5% 6-carboxy-X-rhodamine acid and >95% 6-carboxy-X-rhodamine NHS ester.

EXAMPLE 4

Preparation of R6G-labeled 7-deaza-2',3'-dideoxyadenosine triphosphate (ddA-5R6G)

To 2.0 umoles of amino-7-deaza-2',3'-dideoxyadenosine triphosphate (lyophilized), obtained as described, is added 100 ul of DMF, 3 mg of 5-rhodamine 6G-NHS ester and 50 ul of 1.0 triethylammonium carbonate, pH 8.95. this was vortexed and allowed to stand at room temperature overnight. The mixture was then purified by HPLC on a AX-300 220×4.6 mm, 7 micron column with 1.5 ml per minute flow rate. Starting elution was at 60% 0.1M triethylammonium carbonate, pH 7.0, 40% CH3CN with a linear gradient to 60% 1.2M triethylammonium carbonate, pH 7.5, 40% CH3CH over 40 minutes. The solvent was removed from the collected product by evaporation under vacuum. The residue was dissolved in 0.01M triethylammonium acetate pH 7.0 and quantified.

EXAMPLE 5

Preparation of ROX-labeled 2',3'-dideoxycytidine triphosphate (ddC-6ROX)

To a solution of 5-(3"-amino-1"-propynyl)-2',3'-dideoxycytidine triphosphate, 3.6 umoles in 150 ul of H₂O, obtained as described was added 5 mg of 6-rhodamine X-NHS ester in 60 ul of DMSO and 50 ul of 1.0M triethylammonium carbonate pH 8.95. This was vortexed and allowed to stand at room temperature overnight. The product was purified as in Example 4.

EXAMPLE 6

Preparation of R110-labeled 2',3'-dideoxyinosine triphosphate (ddG-5R110)

To 1.3 umoles of 7-(3"-amino-1"-propynyl)-7-diaza-2',3'-dideoxyguanosine triphosphate (lyophilized), obtained as described, was added 100 ul of DMF, 4 mg of 5-rhodamine 110-NHS ester, and 100 ul of 1.0M triethylammonium carbonate pH 8.95. This was vortexed and allowed to stand overnight at room temperature. The product was purified as in Example 4.

EXAMPLE 7

Preparation of TMR-labeled 2',3'-dideoxythymidine triphosphate (ddT-6TMR)

3.1 umoles of 5-(3"-amino-1"-propynyl)-2',3'-dideoxyuridine triphosphate in 150 ul of H₂O, obtained as described, was mixed with 150 ul of DMF, 100 ul of 1.0M triethylammonium carbonate pH 8.95, and 4 mg of 6-TMR-NHS ester. This was vortexed and allowed to stand overnight at room temperature. The product was purified as in Example 4.

EXAMPLE 8

2',7'-dimethoxy-4',5'-dichloro-5-(and 6-)carboxy-4,7-dichlorofluorescein ("LOU")

0.60 g of 3,6-dichlorotrimetllitic acid, 1.47 g of 4methoxyresorcinol, 0.2 ml concentrated sulfuric acid, and 4 ml of propionic acid were refluxed 12 hours under argon. The reaction mixture was poured into 150 ml water; the precipitate was dried, taken into 3 ml pyridine and acetylated with 2 ml acetic anhydride for 1 hour. The acetylation mixture was taken into 100 ml ethyl acetate, washed with 1N hydrochloric acid, water, and evaporated to dryness. The residue was placed on 15 grams of silica gel and eluted with 50 ml ethyl acetate, then 4:1 ethyl acetate:methanol. Fractions containing UV active material with $R_f$ of about 0.2 (4:1 ethyl acetate: methanol/silica gel) were evaporated to dryness. This residue was dissolved in 10 ml methanol and then 1 ml of 4N sodium hydroxide was added. After 10 minutes, the reaction mixture was diluted to 200 ml with water and then 0.5 ml of concentrated hydrochloric acid was added. The total mixture was extracted with 200 ml of ethyl acetate, after which the ethyl acetate was dried with sodium sulfate and evaporated to dryness yielding 0.180 g of yellow-green solid. This solid was then treated with hypochlorite in aqueous sodium hydroxide to yield LOU.

EXAMPLE 9

1',2',7',8'-dibenzo-5-(and 6-)carboxy-4,7-dichlorofluorescein ("NAN")

First, 3,6-dichlorotrimetllitic acid trichloride was prepared: A mixture of 0.5 g of 3,6-dichlorotrimetllitic acid and 1.3 g of phosphorous pentachloride was heated at 130° C. for 40 minutes. The mixture was cooled to room temperature and poured into ice. The mixture was then extracted with 40 ml ether, the organic fraction was washed twice with 15 ml water, dried with MgSO₄, and concentrated to a clear oil (0.7 g). The acid trichloride was used without further purification. NAN was prepared as follows: A mixture of 2.7 g of 1,3-dihydroxynaphthalene, 2.84 g of 3,6-dichlorotrimetllitic acid trichloride, and 8 ml of propionic acid as refluxed for 2 hours. Water (50 ml) and ethyl acetate (50 ml) were added. The layers were separated and the organic layer was extracted three times with 50 ml of 1M NaHCO₃. The aqueous solution was heated to boiling and acidified with concentrated HCl. The resulting red solid (0.2 g) was filtered and dried.

EXAMPLE 10

DNA sequence analysis using rhodamine-labelled dideoxynucleotides, nucleoside-5'-O-(1-thiotriphosphates), and Sequenase ™ with a Mn⁺⁺ buffer The rhodamine labeled dideoxynucleotides prepared in Examples 6-9 were used to label DNA fragments in chain termination sequencing using an Applied Biosystems (Foster City, Calif.) Model 370A automated DNA sequencer. The manufacturer's protocol (User Bulletin DNA Sequencer Model 370, Issue No. 2, Aug. 12, 1987), which is incorporated by reference, was followed for obtaining M13mp18 single stranded template. (The M13 itself served as a test sequence). The M13 universal primer was employed. The following solutions were prepared: 5X T7 Mn Buffer (100 mM Tris-HCl pH 7.5, 75 mM sodium isocitrate, 10 mM MnCl₂, and 250 mM NaCl); and dNTPaS Mix (500 uM dITPaS, 500 uM dATPaS, 500 uM dTTPaS, and 500 uM dCTPaS, wherein "NTPaS" stands for the 1-thiotriphosphate analog of the indicated nucleotide). The annealing reaction was carried out by combining in a microcentrifuge tube 2.0 ul of 5X T7 Mn buffer, 0.4 pmol DNA template, 0.8 pmol primer, and water to a volume of 4.0 ul. The mixture was incubated at 55°-60° C. for 5-10 minutes, cooled slowly over a 20-30 minute period to a temperature between 4°-20° C., then centrifuged once to collect condensation, mixed, and placed on ice. To the mixture was then added 1.0 ul dNTPaS Mix, ddG-5R110 (0.008 uM); ddA-5R6G (0.1 uM); ddT-6TMR (0.7 uM); ddC-6ROX (1.2 uM); 2 units of Sequenase ™, 1 unit of pyrophosphatase (Sigma Chemical Co.) and water to bring the volume to 10.0 ul. The mixture was incubated for 5 minutes at 37° C., then placed on ice and combined with 25.0 ul of 10 mM EDTA pH 8.0 to quench the reaction. The DNA in the mixture was then ethanol precipitated (by adding 4 ul 3M sodium acetate pH 5.2 and 120 ul 95% ethanol, incubating on ice for 10 minutes, centifuging for 15 minutes, decanting and draining the supernatant, resuspending in 70% ethanol, vortexing, centrifuging for 15 minutes, decanting and draining the supernatant, and drying in a vacuum centrifuge for 5 minutes). The precipitated DNA was then resuspended in 3 ul of a solution consisting of 5 parts deionized formamide and 1 part 50 mM EDTA pH 8.0 and vortexed thoroughly. Prior to loading on the gel the mixture was incubated at 90° C. for 2 minutes to denature the DNA. The base calling routine of the Model 370A sequencer identified 400 bases of the M13 plasmid with 95% accuracy. The incorrect calls were due to missing C's and T's following G's.

EXAMPLE 11

Comparison of fluorescent emission data from electrphoretically separated fluorescein-labelled DNA fragments synthesized with and without nucleoside-5'-O-(1-thiotriphosphates)

Figure 1A:
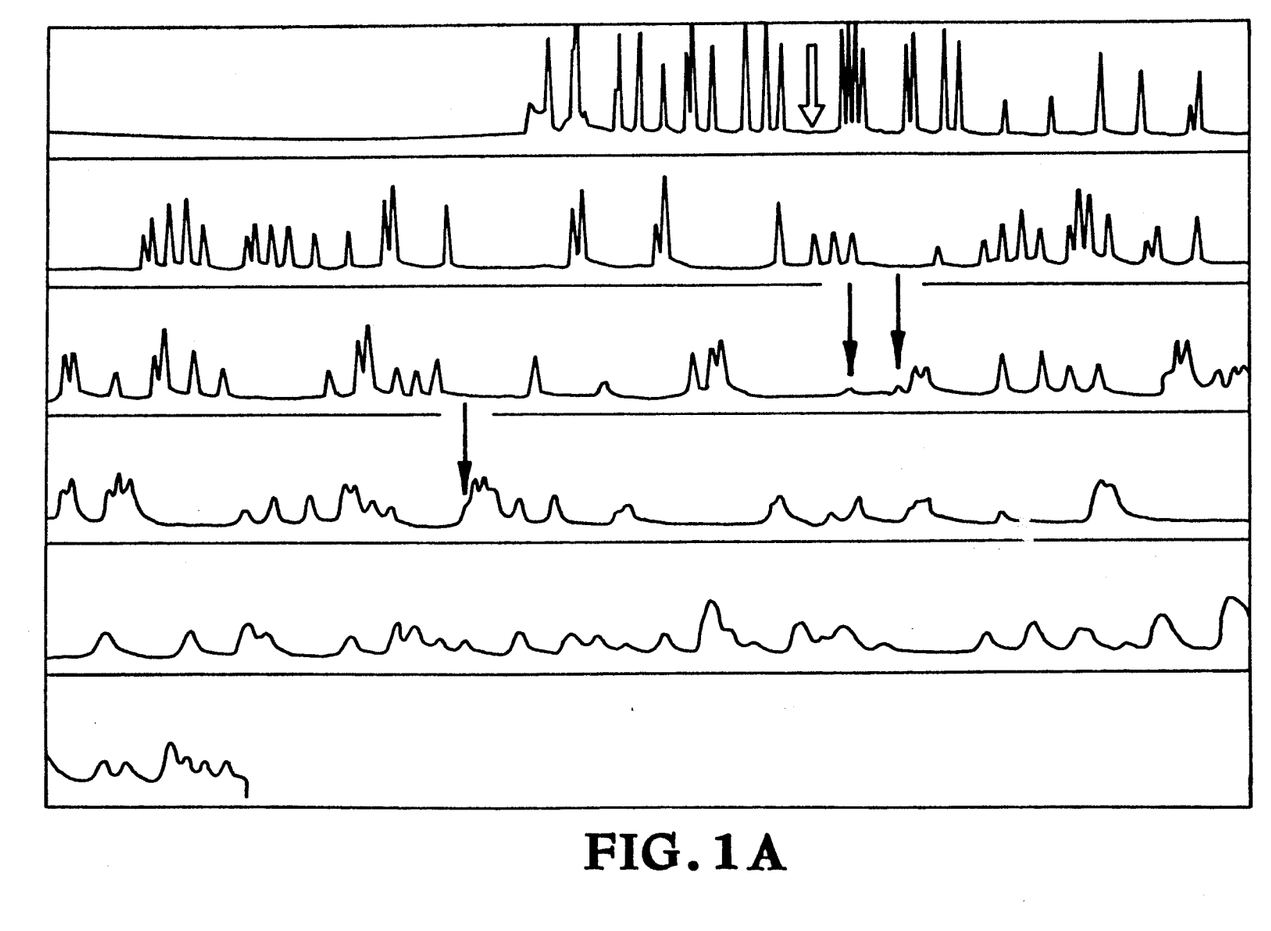
FIGS. 1A and 1B illustrate the fluorescence intensity of bands of DNA fragments polymerized with nucleoside triphosphate precursors (1A) and with nucleoside-5'-O-(1-thiotriphosphate) precursors (1B). The DNA fragments contain terminal dideoxycytidine labelled with 2',7'-dichlorofluorescein.
Figure 1B:
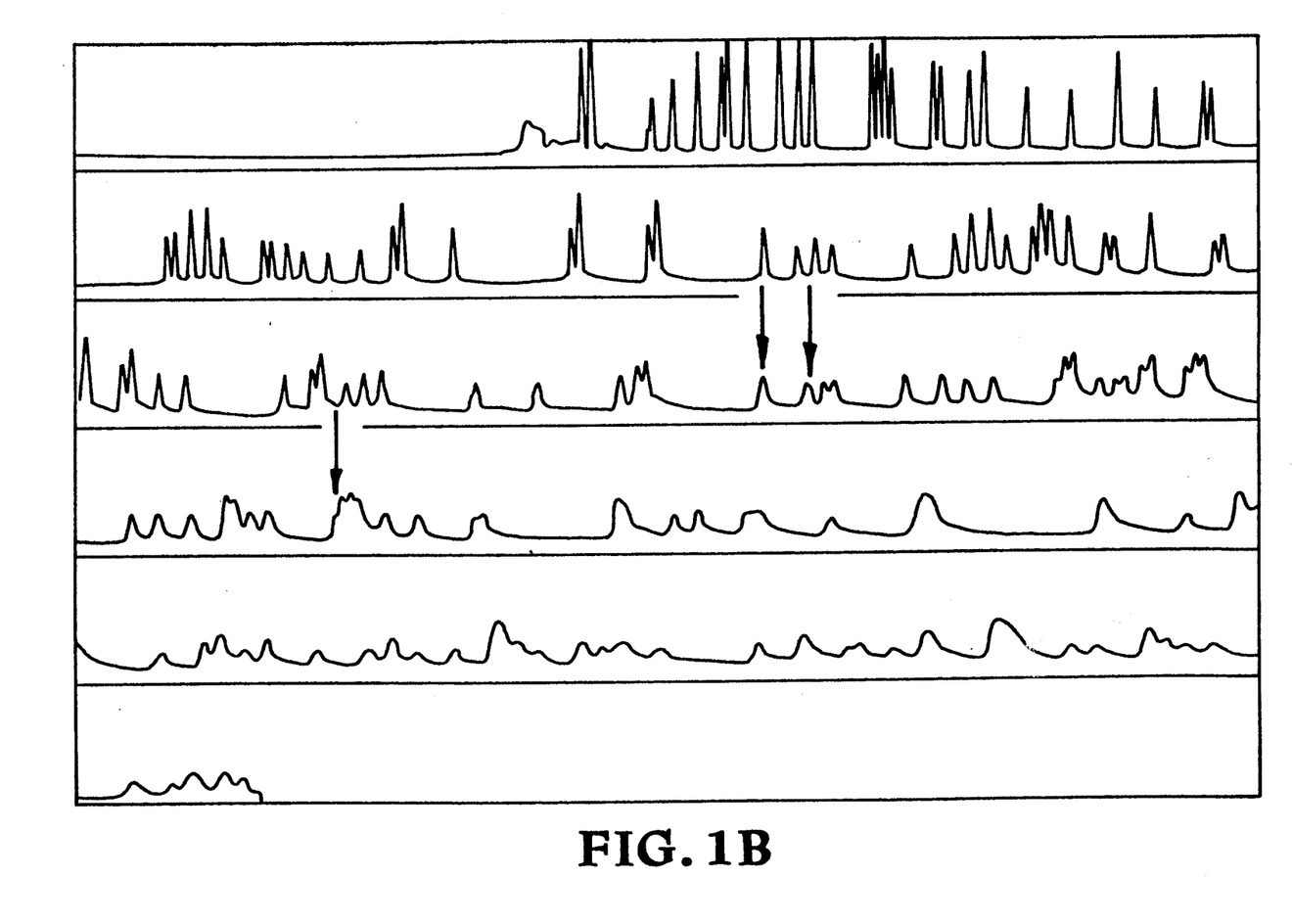
Figure 2A:
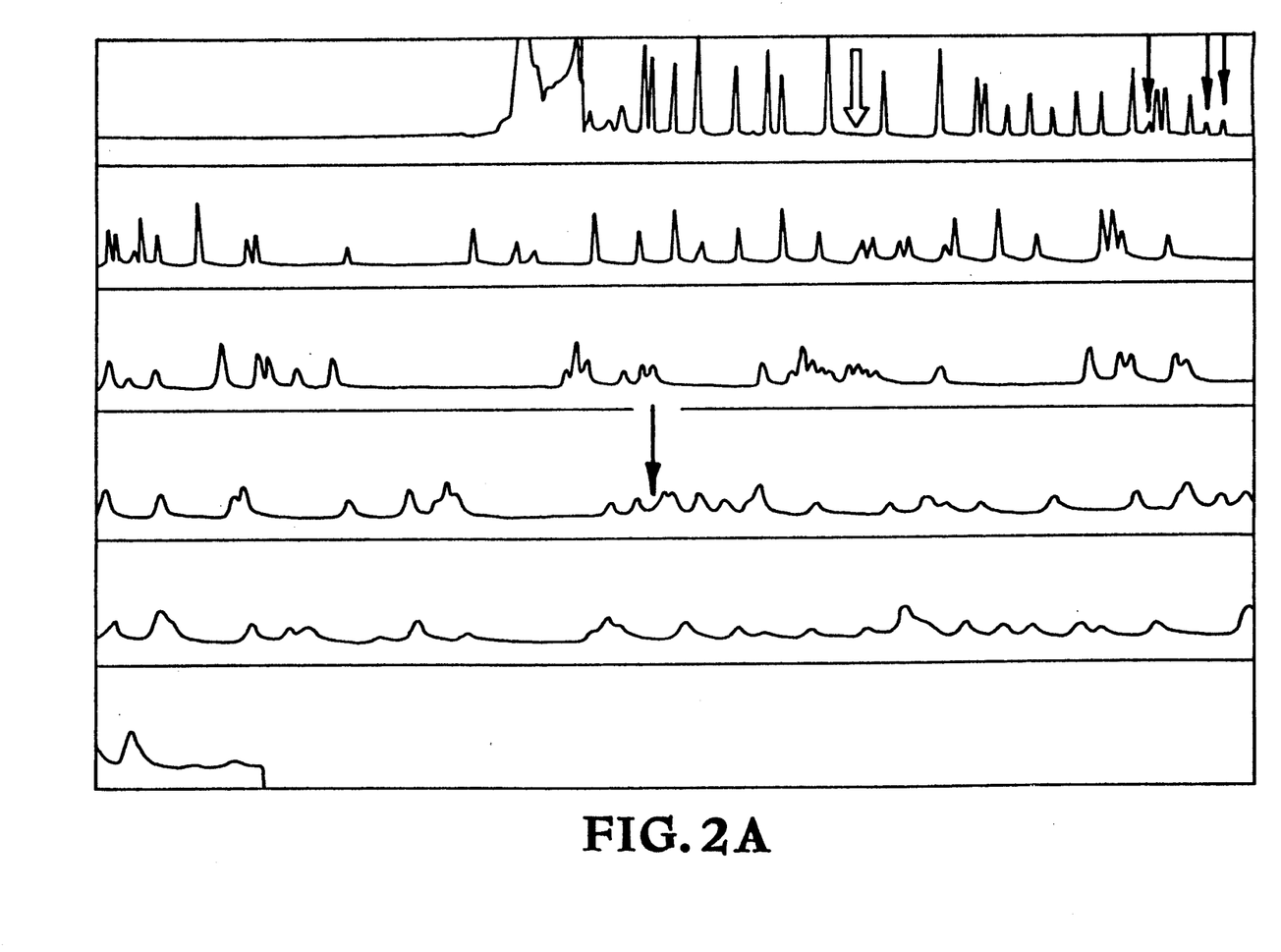
FIGS. 2A and 2B illustrate the fluorescence intensity of bands of DNA fragments polymerized with nucleoside triphosphates precursors (2A) and with nucleoside-5'-O-(1-thiotriphosphate) precursors (2B). The DNA fragments contain terminal dideoxythmyidine labelled with fluorescein.
Figure 2B:
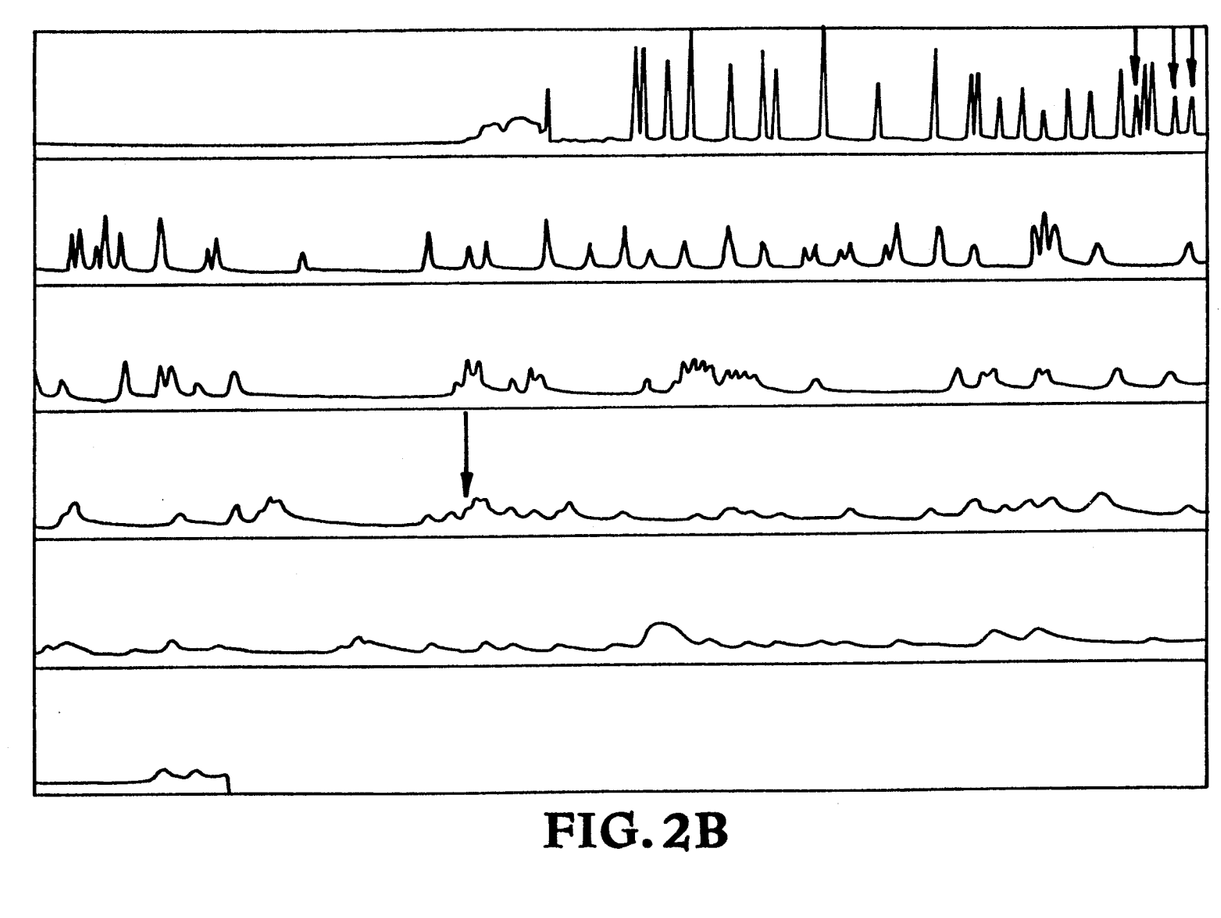

Two pairs of DNA sequence determinations were carried out as described in Example 10 with the following exceptions: (1) in the first pair of sequence determinations only the single fluorescein-labelled dideoxynucleotide, ddT-6-FAM, was employed; in one sequence determination of the pair nucleoside-5'-O-(1-thiotriphosphates) were employed and in the other regular nucleoside triphosphates were employed; (2) in the second pair of sequence determinations only the single fluorescein labelled dideoxynucleotide, ddC-2',7'-dichloro-5-FAM, was employed; and as with the first pair, in one sequence determination nucleoside-5'-O-(1-thiotriphosphates) were employed and in the other regular nucleoside triphosphates were employed. The polymerization reactions contained either nucleoside triphosphates or their 1-thiotriphosphate analogs at 50 uM, and in both cases the fluorescein-labelled dideoxynucleotides at 1.5 uM. FIG. 1A shows the fluorescence intensity generated by bands of ddC-2',7'-dichloro-5-FAM-terminated DNA fragments which were polymerized with the regular nucleoside triphosphate precursors. FIG. 1B shows the fluorescence intensity generated by band of ddC-2',7'-dichloro-5-FAM-terminated DNA fragments which were polymerized with nucleoside-5'-O-(1-thiotriphosphate) precursors. The open arrow indicates a location on the respective traces where the noise level is clearly reduced by the use of the 1-thiotriphosphate analogs. The solid arrows indicate peaks of the respective traces whose resolution is clearly enhanced by the use of the 1-thiotriphosphate analogs. Likewise, FIGS. 2A and 2B show the fluorescence intensities generated by bands of ddT-6FAM-terminated DNA fragments polymerized with regular nucleoside triphosphates (2A) and with nucleoside-5'-O-(1-thiotriphosphates) (2B). Again, the open arrows indicate that less noise is generated when the 1-thiotriphosphate analogs are employed, and the solid arrows indicate the enhanced signal from several bands when the 1-thiotriphosphates analogs are employed.

EXAMPLE 12

Sequence determination with four fluorescein-labelled dideoxynucleotides and nucleoside-5'-O-(1-thiotriphosphates)

A sequence determination was carried out as described in Example 10 with the following exceptions: (1) the following labelled dideoxynucleotides were employed: ddA-5-LOU (0.7 uM), ddC-2',7'-dichloro-5-FAM (0.2 uM), ddG-5-NAN (1.3 uM), and ddT-6-FAM (0.2 uM); and (2) nucleoside-5'-O-(1-thiotriphosphates) were employed in the polymerization reaction at 50 uM. 500 bases were determined with four errors by the 370A automated base-calling routine; 400 bases were determined with complete accuracy.

The foregoing disclosure of preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

We claim:

1. A method of determining the nucleotide sequence of a target nucleic acid, the method comprising the steps of:

providing a template nucleic acid, the template nucleic acid containing the target nucleic acid;

providing an oligonucleotide primer for the template nucleic acid;

hybridizing the oligonucleotide primer to the template nucleic acid;

extending the oligonucleotide primer with a nucleic acid polymerase in a reaction mixture comprising nucleotide precursors and at least one chain-terminating nucleotide to form a nested series of DNA fragment populations such that every DNA fragment of the same size terminates with the same chain-terminating nucleotide, wherein said nucleotide precursors consist of nucleoside-5'-O-(1-thiotriphosphate)s);

separating the DNA fragment populations by size; and identifying the chain-terminating nucleotide associated with each DNA fragment population.

2. The method of claim 1 wherein said step of separating includes separating said DNA fragment populations by gel.electrophoresis to form bands of DNA fragment populations such that each band corresponds to DNA fragments of the same size.

3. The method of claim 2 wherein said at least one chain-terminating nucleotide consists of dideoxyadenosine labelled with a first dye, dideoxycytidine labelled with a second dye, dideoxyguansine labelled with a third dye, and dideoxythymidine labelled with a fourth dye, the first, second, third, and fourth dyes being spectrally resolvable with respect to one another, and wherein said step of identifying includes the steps of illuminating said bands of DNA fragments so that the first, second, third, and fourth dyes are caused to fluoresce, and measuring the fluorescence and/or absorption characteristic of the first, second, third, and fourth dyes.

4. The method of claim 3 wherein said nucleic acid polymerase is Sequenase.

5. The method of claim 4 wherein said dideoxyadenosine is 2',3'-dideoxy-7-deazaadenosine and said first dye is attached by way of a linking group to a 7 carbon atom thereof; said dideoxycytidine is 2',3'-dideoxycytidine and said second dye is attached by way of a linking group to a 5 carbon atom thereof; said dideoxyguanosine is selected from the group consisting of 2',3'-dideoxy-7-deazaguanosine and 2',3'-dideoxy-7-deazainosine and said third dye is attached by way of a linking group to a 7 carbon atom thereof; and said dideoxythymidine is 2',3'-dideoxyuridine and said fourth dye is attached by way of a linking group to a 5 carbon atom thereof.

6. The method of claim 5 wherein said first, second, third, and fourth dyes are selected from the group consisting of rhodamine dyes and fluorescein dyes.

7. The method of claim 6 wherein said linking group is 3-carboxyamino-1-propynyl and links said 7 carbon atoms of said 2',3'-dideoxy-7-deazaadenosine and said dideoxyguanosine selected from the group consisting of 2',3'-dideoxy-7-deazaguanosine and 2',3'-dideoxy-7-deazainosine to a 5 or 6 carbon atom of said first and third dyes, respectively, and links said 5 carbon atoms of said dideoxycytidine and said dideoxythymidine to a 5 or 6 carbon atom of said second and fourth dyes, respectively.

8. The method of claim 7 wherein said first, second, third, and fourth dyes are selected from the group consisting of rhodamine X, tetramethylrhodamine, rhodamine 110, and rhodamine 6G.

9. The method of claim 8 wherein said 2',3'-dideoxy-7-deazaadenosine is attached to said 5 carbon atom of rhodamine 6G, said 2',3'-dideoxycytidine is attached to said 6 carbon atom of rhodamine X, said dideoxyguanosine selected from the group consisting of 2',3'-dideoxy-7-deazaguanosine and 2',3'-dideoxy-7-deazainosine is attached to said 5 carbon atom of rhodamine 110, and said 2',3'-dideoxyuridine is attached to said 6 carbon atom of tetramethylrhodamine.

10. The method of claim 7 wherein said first, second, third, fourth dyes are selected from the group consisting of 5-(and 6-)carboxyfluorescein, 2',7'-dichloro-5-(and 6-)carboxyfluorescein, 2',7'-dimethoxy-4',5'-dichloro-5-(and 6-)carboxy-4,7-dichlorofluorescein, and 1',2',7',8'-dibenzo-5-(and 6-)carboxy-4.7-dichlorofluorescein.

11. The method of claim 10 wherein said 2',3'-dideoxy-7-deazaadenosine is attached to said 5 carbon atoms of 2',7'-dimethoxy-4',5'-dichloro-4,7-dichlorofluorescein, said 2',3'-dideoxycytidine is attached to said 5 carbon atom of 2',7'-dichlorofluorescein, said dideoxyguanosine selected from the group consisting of 2',3'-dideoxy-7-deazaguanosine and 2',3'-dideoxy-7-deazainosine is attached to said 5 carbon atom of 1',2',7',8'-dibenzo-4,7-dichlorofluorescein, and said 2',3'-dideoxyuridine is attached to said 6 carbon atom of fluorescein.

12. The method of claim 1 wherein said steps of providing said template nucleic acid, providing said oligonucleotide primer, hybridizing, and extending include providing an oligonucleotide primer for said template nucleic acid in each of four separate reaction mixtures and separates extending the oligonucleotide primers to form four nested series of DNA fragment populations.

13. The method of claim 12 wherein said DNA fragment populations are radioactively labelled, and wherein said step of separating includes separating by gel electrophoresis each of said four DNA fragment populations to form separate sets of bands of DNA fragment populations such that each band corresponds to DNA fragments of the same size.

14. The method of claim 12 wherein each of said oligonucleotide primers has a label.

15. The method of claim 14 wherein said label for each of said oligonucleotide primers is different.

16. The method of claim 15 wherein said label is selected from a set of spectrally resolvable fluorescent dyes.

17. In a method of determining the nucleotide sequence of a target nucleic acid, the method of the type wherein a nested series of DNA fragment populations is generated by extending an oligonucleotide primer with a nucleic acid polymerase in the presence of one or more chain-terminating nucleotides and wherein the nested series of DNA fragment populations is separated by size, an improvement comprising:
extending the oligonucleotide primer with the nucleic acid polymerase in a reaction mixture comprising nucleotide precursors consisting of nucleoside-5'-O-(1-thiotriphosphate)s.

18. The method of claim 17 wherein said DNA fragment populations are separated by gel electrophoresis.

19. The method of claim 18 wherein said one or more chain-terminating nucleotides consist of dideoxyadenosine labelled with a first fluorescent dye, dideoxycytidine labelled with a second fluorescent dye, dideoxyguanosine labelled with a third fluorescent dye, and dideoxythymidine labelled with a fourth fluorescent dye, the first, second, third, and fourth fluorescent dyes being spectrally resolvable with respect to one another.

20. The method of claim 19 wherein said nucleic acid polymerase is Sequenase.

* * * * *